United States Patent
Vincent et al.

(10) Patent No.: US 8,873,044 B2
(45) Date of Patent: Oct. 28, 2014

(54) APPARATUS AND METHODS FOR OPTICAL EMISSION SPECTROSCOPY

(75) Inventors: Francois Vincent, Cugy (CH);
Jean-Pierre Sola, Carrouge (CH);
Gilbert Wuethrich, Le Mount-sur-Lausanne (CH)

(73) Assignee: Thermo Fisher Scientific (Ecublens) Sarl, Ecublens (CH)

( * ) Notice: Subject to any disclaimer, the term of this patent is extended or adjusted under 35 U.S.C. 154(b) by 78 days.

(21) Appl. No.: 13/129,785

(22) PCT Filed: Dec. 4, 2009

(86) PCT No.: PCT/EP2009/066420
§ 371 (c)(1),
(2), (4) Date: May 17, 2011

(87) PCT Pub. No.: WO2010/066644
PCT Pub. Date: Jun. 17, 2010

(65) Prior Publication Data
US 2011/0228269 A1   Sep. 22, 2011

(30) Foreign Application Priority Data
Dec. 10, 2008 (GB) .................................. 0822495.8

(51) Int. Cl.
*G01J 3/30* (2006.01)
*G01J 3/443* (2006.01)
*H03K 3/57* (2006.01)

(52) U.S. Cl.
CPC .. *G01J 3/443* (2013.01); *H03K 3/57* (2013.01)

USPC .......................................................... 356/313

(58) Field of Classification Search
USPC .......................................................... 356/313
See application file for complete search history.

(56) References Cited

U.S. PATENT DOCUMENTS 4,898,466 A * 2/1990 Fukui et al. .................. 356/313

FOREIGN PATENT DOCUMENTS

| | | |
|---|---|---|
| EP | 0 084 566 A1 | 2/1983 |
| EP | 0 318 900 A2 | 6/1989 |
| EP | 0 396 291 A2 | 11/1990 |
| JP | 1-229942 | 9/1989 |
| JP | 2-297046 | 12/1990 |
| JP | 08159973 A | 6/1996 |
| JP | 8-210980 | 8/1996 |
| JP | 3511707 B2 | 1/2004 |

\* cited by examiner

*Primary Examiner* — Abdullahi Nur
(74) *Attorney, Agent, or Firm* — Gordon Stewart (57) ABSTRACT

The invention provides a spark generator for generating a spark for optical emission spectroscopy (OES), wherein the spark has a current waveform comprising a first modulated portion which comprises a plurality of relatively high current and high gradient peaks of variable amplitude and/or inter-peak duration and a second modulated portion of relatively low current and low gradient which is substantially without modulated peaks. The spark is preferably generated from two or more programmable current sources. The invention also provides an optical emission spectrometer comprising the spark generator and a method of optical emission spectroscopy using the spark generator.

30 Claims, 7 Drawing Sheets

APPARATUS AND METHODS FOR OPTICAL EMISSION SPECTROSCOPY

FIELD OF THE INVENTION

The present invention relates to apparatus and methods for optical emission spectroscopy, in particular, but not exclusively, to a spark generator, a spectrometer and a method for optical emission spectroscopy.

BACKGROUND OF THE INVENTION

Optical emission spectroscopy (OES), also termed atomic emission spectroscopy (AES), is a technique for the elemental analysis of samples and is particularly useful, for example, in the analysis of solid, metallic samples. The present invention relates to OES wherein a spark (herein used to refer to any electrical spark, arc or discharge) is used to rapidly vaporise a sample and excite elements in the vapourised sample, i.e. so-called spark OES. Light is emitted by the excited elements of the sample as transitions occur from an excited state to a lower energy state. Each element emits light of discrete wavelengths characteristic of its electronic structure, which are also termed spectral lines. By detecting the spectral lines, OES can provide a qualitative and quantitative determination of the elemental composition of the sample. A spark optical emission spectrometer thus includes a spark generator for exciting the elements in the sample to emit light, an optical system for dispersing the emitted light into discrete wavelengths, a detection system for detecting the light intensity of the dispersed light and a data storage and processing system for storing and processing signals from the detection system representing the light intensity. To build up sufficient data for determination of the composition, a succession of sparks is typically employed and the resulting data generated from the sparks is accumulated for processing.

A spark generator for producing a sequence of sparks for exciting a sample in OES should preferably produce sparks having a stable energy output and high degree of reproducibility for high accuracy of measurements.

Conventional analogue spark generators, in which sparks are generated in an unmodulated way by the discharge of a capacitor through a resistance and an inductance (RLC circuit), do not permit a high amount of control over the current waveform or profile of the spark and hence the reproducibility is low. Accordingly, the accuracy of measurement of components in a sample is adversely affected. The current waveform of an analogue spark source is generally characterised by a relatively slow rise of the spark current (compared to the digital sources described below) to a broad peak before a gradual fall or decay of the current in an exponential manner over a longer time period. It has been found that this type of unmodulated current profile is not well suited to the analysis of trace elements in samples. Although it may be better for analysis of alloying elements in metals than trace elements, even in that case the analogue generated spark still leads to the poor measurement accuracy mentioned above due to poor spark reproducibility.

So-called digital spark generators, e.g. as described in EP 396 291 B1, which generate modulated sparks are known and these have sought to address some of the above issues. In that reference is described a spark generator including means for measuring the spark current during the spark, comparing the spark current to a reference current and adjusting the spark current to a pre-determined value dependent on the reference current. The sampling rate for the reference comparison is said to be 50-200 kHz. The reference current is stored on a computer as part of a program for the spark current waveform. The modulated current waveform described in the prior art generally has a single initial peak of high amplitude (high current) and of relatively short duration followed by a longer lasting modulated decay of low current, which resembles something of a current plateau. The high amplitude peak may be a factor of 5 more intense than the current plateau. Such a waveform is shown schematically in FIG. 4 of EP 396 291 B1. The initial high current peak is described as being mainly for use in the evaporation of the sample and the longer lasting current is for exciting the atoms in the vapourised sample. It has been found that this type of current profile is better than the profile of the analogue spark source for detecting trace elements but is not so well suited to the analysis of alloying elements in metal alloy samples.

In JP 8-159973 A and EP 318 900 A2, another type of spark source is described in which two portions of current are produced. A high current portion is produced first which is a single peak and a low current portion is produced second which comprises two or three peaks of progressively lower intensity. These spark sources suffer from a lack of control due to the use of passive circuitry. In particular, the amplitudes and durations of current peaks are fixed by different values of capacitors and inductors. In EP 84566 A is disclosed a spark source employing a decaying oscillatory current source again employing passive circuitry (i.e. a resonant LC circuit) and therefore also suffers from a lack of control. The current envelope simply decreases along an exponentially decaying curve with peak frequency being determined by the resonant frequency of the circuit.

An additional problem with OES instruments employing charge coupled device (CCD) detectors as light detectors is that such detectors can exhibit deterioration in their response over time. It would be desirable to reduce the rate of such deterioration.

In view of the above background, the present invention has been made.

SUMMARY OF THE INVENTION

According to the present invention there is provided a spark generator for generating a spark for optical emission spectroscopy (OES), wherein the spark has a current waveform comprising a first modulated portion which comprises a plurality of relatively high current and high gradient peaks of variable amplitude and/or inter-peak duration and a second modulated portion of relatively low current and low gradient which is substantially without modulated peaks.

According to another aspect of the present invention there is provided an optical emission spectrometer comprising the spark generator according to the present invention.

The spark generator and the optical emission spectrometer according to the present invention are preferably for carrying out the method according to the present invention described below.

According to a further aspect of the present invention there is provided a method of optical emission spectroscopy comprising:

generating a spark between an electrode and a sample to be analysed, the spark having a current waveform comprising a first modulated portion which comprises a plurality of relatively high current and high gradient peaks of variable amplitude and/or inter-peak duration and a second modulated portion of relatively low current and low gradient which is substantially without any modulated peaks;

dispersing light emitted by the sample as a result of the spark; and detecting the intensity of the dispersed light at selected wavelengths.

Preferably, the spark is produced in the method by the spark generator according to the present invention. Also preferably, the method is performed by the optical emission spectrometer according to the present invention.

The present invention has numerous advantages including those now specifically described. Other advantages will be apparent from the description below. The present invention allows a more controlled separation in time of the different phases in the spark process. For example, the invention allows a better separation of the phase of pre-treatment (re-melting and structure refining) and vaporisation of the sample surface from the phase of excitation of the resultant vapours for optical analysis. The use of programmable current sources permits variation of the inter-peak duration, the rise time, the peak amplitude and the number of high current peaks. This degree of control is not possible with either the cascaded current sources of JP 8-159973 A and EP 318 900 A2 or the decaying oscillatory current source of EP 84566 A.

The use of a first modulated current portion comprising a plurality of relatively high current and high gradient peaks has been found to allow a better control of the high energy delivery to the sample surface. This high energy delivery conditions and vaporises the sample surface in a better controlled way than a single high current peak at the beginning of the spark. More specifically, this feature allows controlling separately the magnitude of the spark plasma energy (i.e. temperature) and duration of this energy transfer to the sample surface, during the high energy phase. In more detail but without the scope of the invention being bound by any theory, modulating the energy delivered to the spark in the claimed way allows alternating rapidly between a high energy plasma stage for vaporizing and a lower energy stage which promotes stabilization phenomena at the sample surface while allowing the highest energies of the vapours to relax for optimising the forthcoming analysis phase.

The use of a second modulated current portion of relatively low current substantially without modulation peaks, which can even be in the form of a current plateau, cannot be achieved by the devices described in JP 8-159973 A, EP 318 900 A2 and EP 84566 A because the electrical circuits employed in those devices are intrinsically designed to deliver current pulses and are not able to maintain a current plateau. This feature of the present invention instead is provided by a programmable current source. Preferably, the relatively low current portion of the invention is not a vanishing current but a stabilized and controlled current. The aim of this is to provide the spark with a limited and controlled amount of energy to optimize the excitation of vapours for analysis. In this analytical phase, the energy level and the duration of this energy supply to the vapours can be controlled separately using the present invention.

The invention enables the determination with good precision of both trace elements and alloying elements in metal samples, in contrast to the prior art methods described above which are better suited to either one of these applications or the other. As with other spark sources, a part of the spark's energy will be used for sample evapouration, a part for atomisation and/or ionisation and a part for excitation However, without the scope of the present invention being bound by any particular theory, the invention may achieve the advantage above because the spark energy is delivered in a plurality of relatively high current high gradient current peaks (i.e. high energy), e.g. in the early part of the waveform, compared to the purely analogue spark source, thus creating more controlled higher temperature zones in the plasma, e.g. which may be of 7,000-10,000K, which favour high energy electron transitions in atomic and ionic species. The most sensitive spectral lines, which can be useful in determining trace elements, typically arise from the so-called resonance transitions, such as atomic type transitions (described in tables of spectral lines as U1, U2, . . . etc.) and ionic type transitions (described in tables of spectral lines as V1, V2, . . . etc.). These have high transition probabilities and can have high energies, e.g. in the range of 7 to 12 eV, and thus are most efficiently excited by the high temperature plasma. In particular, the use of a plurality of peaks in the high current part of the waveform, which is preferably programmable, of variable amplitude and/or inter-peak duration gives a better degree of control of the duration of the high temperature plasma.

Similarly, without the scope of the invention being bound by any theory, the detection of alloying elements in metals may be enhanced, compared to the prior art digital spark source described in EP 396 291 B1, because the spark energy is not concentrated into a single, highly intense current peak at the beginning of the waveform but instead is spread over a plurality of peaks of variable amplitude and/or inter-peak duration so that the waveform is also efficient at promoting lower energy electron transitions (e.g. 2 to 7 eV) which tend to occur later in the spark, mainly in atomic species, and it creates a lower background for these transitions. These types of atomic transitions are often less sensitive, i.e. having lower transition probabilities, and as such can be useful in determining alloying elements which otherwise would, due the high concentration of the elements present, produce highly intense spectral lines that could overload the detector.

Due to the improved control over the energy delivery to the spark plasma, a better time separation of the excitation conditions favourable for high energy transitions (e.g. 7-12 eV) on the one hand and the excitation conditions favourable for low energy transitions (e.g. 2-7 eV) on the other can be achieved with the present invention. The invention also allows better separation of the spectral background (also termed continuum radiation) from the useful transitions. These features benefit the use of so-called "time-resolved spectroscopy" (TRS) often used in OES in which the emitted light is measured only within a defined time window located within the spark duration. TRS may also be termed Time Gated Spectroscopy (TGS). Different time windows can be employed in TRS for different spectral lines. The choice of time window depends on the parameters of the spectral line such as its energy. The time window can also be chosen to minimise perturbations to the spectral line from, e.g., the source or spectral background interference. TRS is, for example, of significant benefit for trace element analysis.

The present invention has been found to significantly improve precision in the quantitative determination of many compositions (for a given acquisition time) and thereby reduce acquisition times for the same precision.

The use of a spark having a waveform in accordance with the present invention can reduce the rate of deterioration of the response of a CCD light detector in the environment of an OES instrument. Without being bound by any theory, it is believed that the deterioration is due to a photochemical reaction ("quenching") of volatile organic molecules, which are typically present in the low pressure environment of the instrument in small amounts, with intense UV light, such as is produced when using the single intense current peak of the prior art digital spark source. The photochemically produced products are then thought to become deposited on the surface of the CCD detector, which lowers the detector sensitivity over time. The present invention uses a spark which spreads the high energy over a plurality of peaks of variable amplitude and/or inter-peak duration rather than concentrate the energy into the single intense peak as in the prior art and this is believed to reduce the quenching probability and thereby explaining the observed reduction of the deposition rate on the detector when used with the present invention.

BRIEF DESCRIPTION OF THE DRAWINGS

The invention will now be described in more detail by way of examples and with reference to the accompanying drawings in which.

It will be appreciated that the embodiments shown in the Figures are non-limiting on the scope of the invention and are examples intended for illustration only.

DETAILED DESCRIPTION OF EMBODIMENTS OF INVENTION

Figure 1:
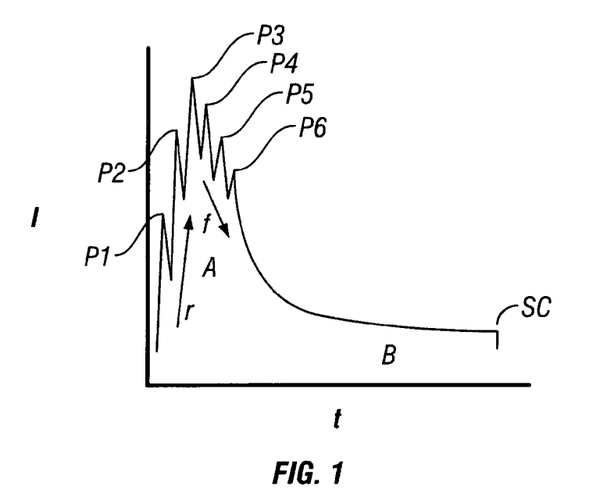
FIG. 1 shows schematically an example of a spark current waveform generated by a spark generator according to the present invention.
Figure 2A:
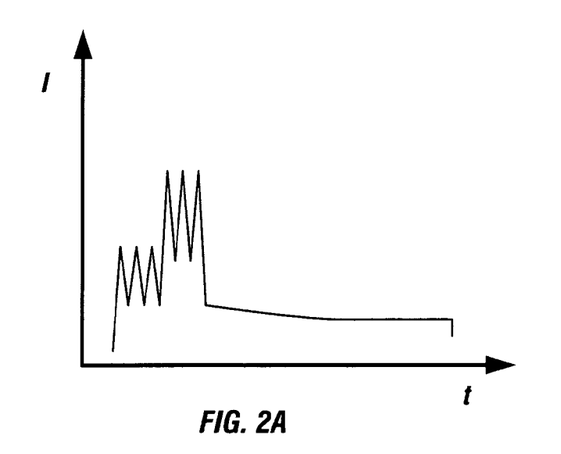
FIG. 2A shows schematically a second example of a spark current waveform generated by a spark generator according to the present invention.
Figure 2B:
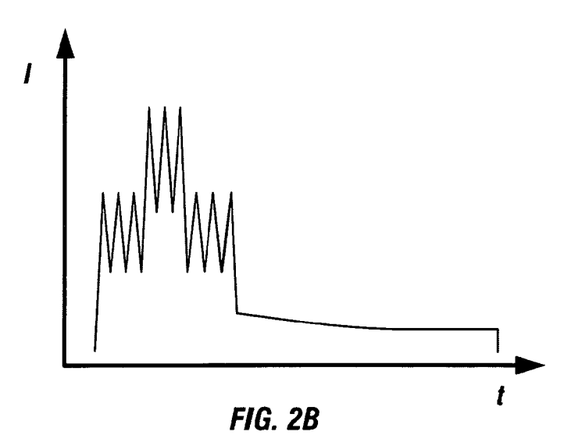
FIG. 2B shows schematically a third example of a spark current waveform generated by a spark generator according to the present invention.
Figure 2C:
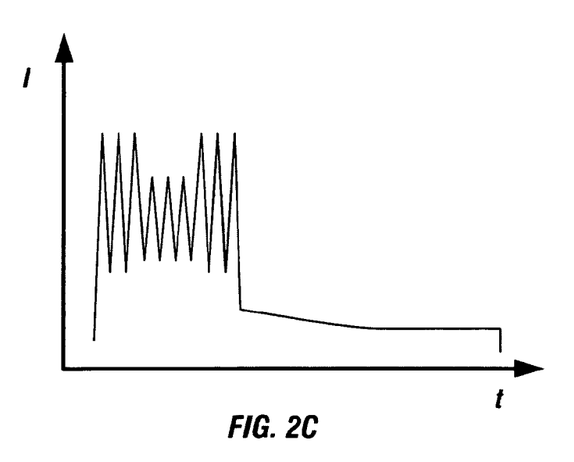
FIG. 2C shows schematically a fourth example of a spark current waveform generated by a spark generator according to the present invention.
Figure 2D:
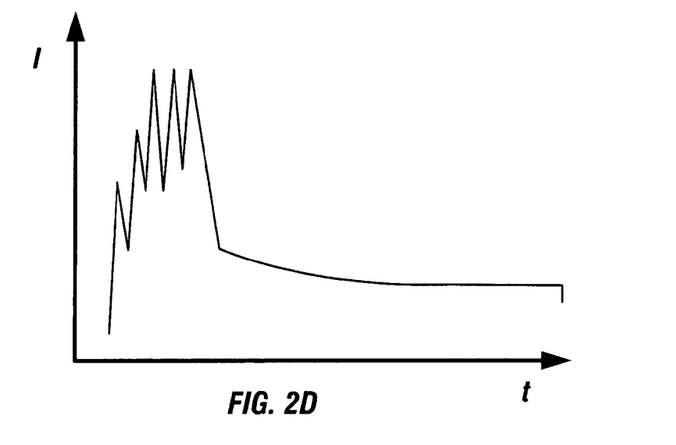
FIG. 2D shows schematically a fifth example of a spark current waveform generated by a spark generator according to the present invention.
Figure 2E:
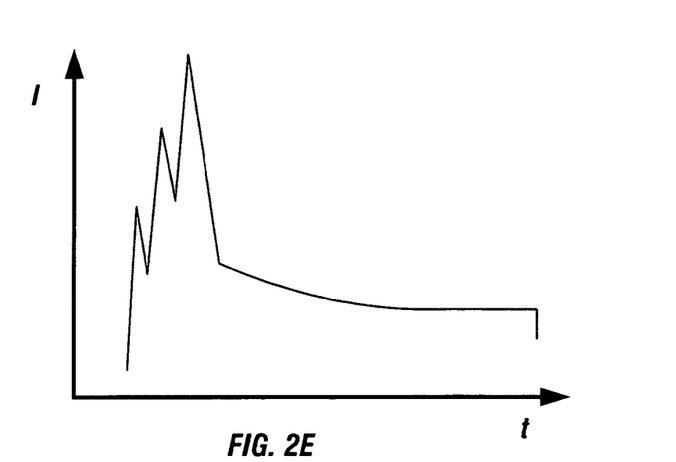
FIG. 2E shows schematically a sixth example of a spark current waveform generated by a spark generator according to the present invention.

One example of a current waveform according to the present invention is shown schematically in FIG. 1. FIG. 1 plots the spark current (I) against time (t). It can be seen from FIG. 1 that the waveform comprises a modulated waveform comprising a first modulated portion of relatively high current denoted by A followed by a second modulated portion of relatively low current denoted by B. The term relatively as used herein, e.g. relatively high current or gradient or relatively low current or gradient, means relative to the other, e.g., current or gradient. For example, the term relatively high current means a higher current relative to the relatively low current. It will be appreciated that, alternatively to the waveform shown in FIG. 1, in some embodiments the first modulated portion of the waveform may follow the second modulated portion of the waveform in time. Accordingly, the terms first modulated portion and second modulated portion herein do not denote an order in time but rather just denote two different portions of modulation. However, preferably, the first modulated portion of the waveform is first in time, i.e. the first modulated portion is followed by the second modulated portion of the waveform. Such embodiments allow the relatively higher current of the first modulated portion to be utilised in the evapouration of the sample.

The relatively high current portion A is characterised by being modulated by a plurality of relatively high gradient peaks, labelled as P1-P6 in this example, of variable amplitude and/or inter-peak duration. In FIG. 1, the case of modulation by a plurality of peaks of variable amplitude is shown. The sequence of peaks P1-P3 represents modulation of a steep leading edge or current rise (represented by upward arrow r in FIG. 1) of the high current portion A by relatively high gradient peaks of increasing amplitude. The sequence of peaks P3-P6 represents further modulation of the high current portion A by relatively high gradient peaks of decreasing amplitude, which modulate a trailing edge or current fall (represented by the downward arrow f in FIG. 1) of the high current portion A. Accordingly, it can be seen that in one type of embodiment of the present invention, the first portion (i.e. relatively high current portion) of the waveform comprises an underlying current envelope, i.e. comprising a current rise and a current fall. In such embodiments, the current rise may be modulated by a plurality of relatively high gradient peaks of increasing amplitude and the current fall may be modulated by a plurality of relatively high gradient peaks of decreasing amplitude. In other embodiments, other modulations are possible. For example, in some embodiments, only the current rise of the first portion of the waveform may be modulated by a plurality of the relatively high gradient peaks (preferably of increasing amplitude) with the current fall not having a plurality of relatively high gradient peaks, or vice versa. Preferably, at least the current rise of the first portion of the waveform is modulated by a plurality of the relatively high gradient peaks of variable amplitude and/or inter-peak duration (preferably of increasing amplitude).

It will be appreciated that other modulations of the waveform than that shown in FIG. 1 are possible within the scope of the present invention. For example, the sequence of relatively high gradient modulated peaks may be varied.

Figure 3A:
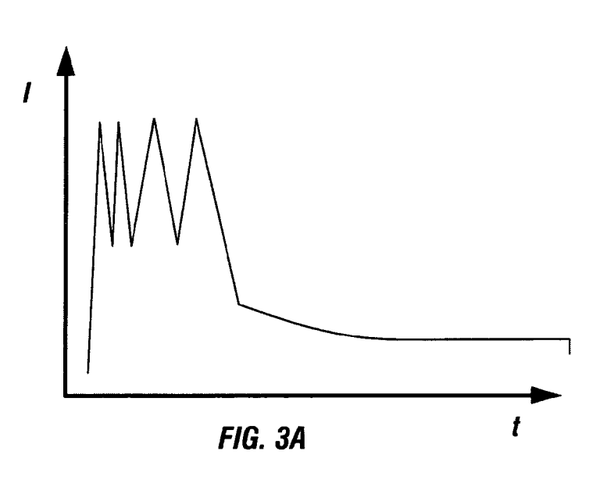
FIG. 3A shows schematically a seventh example of a spark current waveform generated by a spark generator according to the present invention.
Figure 3B:
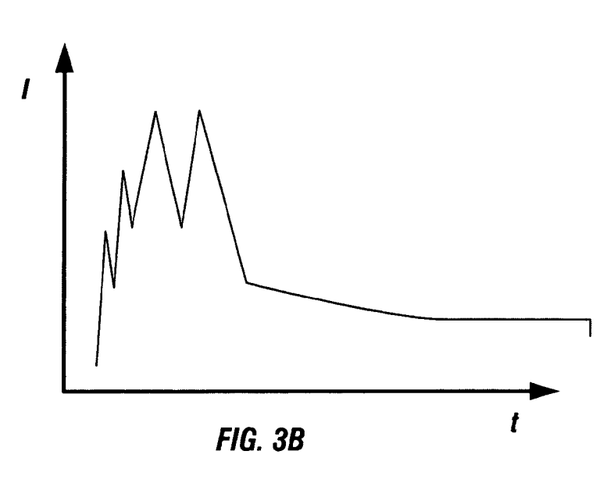
FIG. 3B shows schematically an eighth example of a spark current waveform generated by a spark generator according to the present invention.

In some embodiments, the first relatively high current portion (i.e. first modulated portion) of the waveform may be modulated by at least a plurality of relatively high gradient peaks of a first high amplitude and a plurality of relatively high gradient peaks of a second high amplitude. For example, the first relatively high current portion of the waveform may be modulated by a plurality of relatively high gradient peaks of a first high amplitude, followed by a plurality of relatively high gradient peaks of a second high amplitude, optionally followed by a plurality of relatively high gradient peaks of a third high amplitude, which may be the same as the first high amplitude again or a different high amplitude and so on until the relatively low current portion of the waveform. Schematic representations of various spark current waveforms according to the present invention having relatively high current high gradient peaks of variable amplitude are shown in FIGS. 2A to 2E. In FIGS. 3A and 3B are shown schematic representations of examples of spark current waveforms according to the present invention having relatively high gradient peaks of variable inter-peak duration (FIG. 3A) and of variable amplitude and variable inter-peak duration (FIG. 3B).

Figure 4:
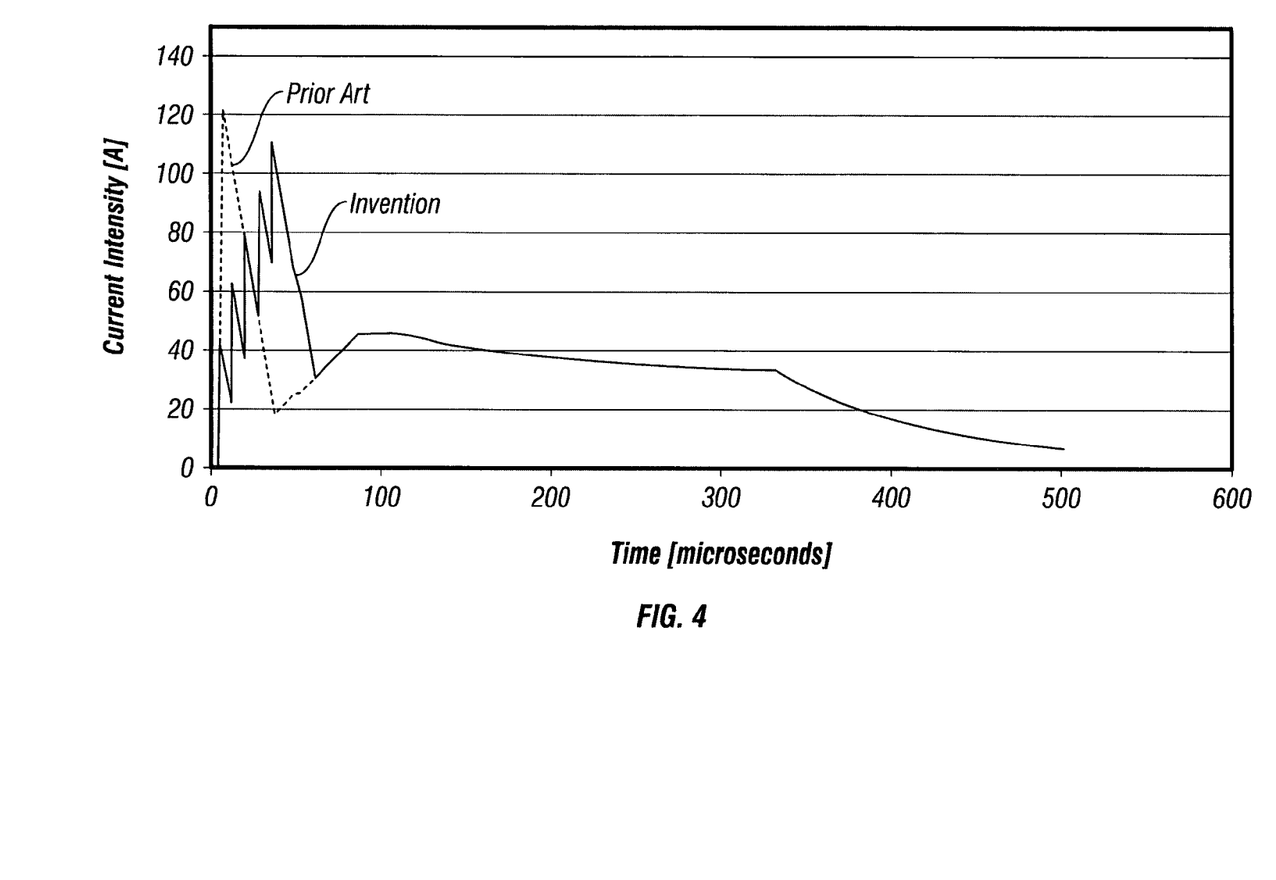
FIG. 4 shows a comparison of a spark waveform according to the present invention with a spark waveform according to the prior art.

A comparison of a spark of the present invention with a prior art single peak spark is shown in the example in FIG. 4, in which it can be seen that the energy of the spark of the present invention is spread across several peaks in the case of the present invention thereby giving better overall control of the spark energy delivery with respect to amplitude and time. In the low current portion, the two waveforms are superimposed.

The second relatively low current portion of the waveform (i.e. second modulated portion), e.g. denoted by B in FIG. 1, in the embodiment shown follows the modulation by the plurality of relatively high gradient peaks and preferably is in the form of a longer lasting current (i.e. longer duration than the first relatively high current portion). Preferably, the relatively low current portion is modulated by a relatively low gradient low current which tends toward a current plateau (i.e. a substantially constant current value). The plateau is preferably a non-zero plateau. This provides that a limited and controlled amount of energy is provided by the second current portion.

In some embodiments, the second relatively low current portion (i.e. second modulated portion) may be modulated by a relatively low gradient current which modulation is stopped after a pre-determined time such that the low current portion then follows an unmodulated decay, e.g. as results from exponential decay, in a third portion. At the end of the relatively low current portion, the current waveform is preferably interrupted, e.g. by a short circuit, to terminate the discharge abruptly to reduce afterglow arcing. Such an interruption is shown, for example, in FIG. 1 at point SC.

The relatively low current and low gradient portion (i.e. second modulated portion) is preferably substantially without any modulated peaks, thus including substantially without relatively high gradient peaks. In this way, the relatively low current portion preferentially excites lower energy atomic transitions, thereby allowing better time separation of these transitions from the higher energy transitions which are preferentially excited by the relatively high current portion of the spark.

By employing a spark with a current waveform comprising a plurality of relatively high gradient peaks of variable amplitude and/or inter-peak duration, in conjunction with the modulated relatively low current second portion of low gradient, the present invention enables a range of different types of transitions, both atomic and ionic, and both high energy and low energy, to be efficiently excited such that the invention is effective at measuring both trace elements and alloying elements in metallic samples. The plurality of relatively high gradient peaks may have their variable amplitudes and/or inter-peak durations programmed to suit a particular analytical application, e.g. the waveform may be tailored to one which is effective for measuring the target elements in a given sample. Similarly, the modulated low gradient of the second relatively low current portion may be programmed to suit the particular analytical application.

The relatively high gradient peaks of variable amplitude and/or inter-peak duration may have either variable amplitudes or variable inter-peak duration (i.e. different time intervals between the peaks) or both. Preferably, the peaks are at least of variable amplitude (i.e. optionally with variable inter-peak duration).

In general, the high gradient current peaks of the waveform may be modulated in terms of their number, their amplitude and/or their inter-peak duration to suit a particular analytical application. The number of peaks, their amplitude and/or inter-peak duration are preferably programmable and controlled by a computer which controls the spark generator circuit as described in more detail below.

As used herein, the term plurality in relation to the number of current peaks means two or more. The number of peaks in the waveform may be programmed to suit the sample to be analysed. Typically, the composition constituting the matrix of the sample, e.g. in a metal sample, is a significant factor in determining the number of peaks in the modulation. Thus, the optimum number of peaks may be experimentally determined and then an appropriate computer program or parameters for a computer program controlling the peak modulation may be selected accordingly.

Preferably, the first relatively high current modulated portion is modulated by two or more peaks of variable amplitude and/or inter-peak duration, more preferably three or more. For example, the waveform may be programmed to have four, five, six, seven or more peaks. For example, FIG. 1 shows a waveform according to the present invention having, in its relatively high current portion, three peaks on the current rise and four peaks on the fall (counting the highest peak as part of the rise and the fall) and six peaks in total.

The first relatively high current modulated portion of the waveform generally comprises a leading edge or rise of the spark current, e.g. rise r shown in FIG. 1. This leading edge preferably is modulated by a plurality of the relatively high current high gradient peaks, more preferably of increasing amplitude, more preferably at least three such peaks of increasing amplitude. The relatively high current portion of the waveform preferably also comprises a trailing edge or fall, e.g. fall f shown in FIG. 1. This trailing edge preferably is modulated by a plurality of the relatively high gradient peaks, more preferably of decreasing amplitude, more preferably at least 2 such peaks of decreasing amplitude.

The term variable amplitude in relation to the plurality of relatively high gradient current peaks means that the peaks are not all of the same amplitude and the amplitude of each peak may be independently adjusted, e.g. according to a modulation program. For example, the amplitude of each peak may be dependent on one or more reference currents of a modulation program, as described in detail below. In some embodiments, the high gradient current peaks may each be of different amplitude. In other embodiments, two or more of the plurality of relatively high gradient current peaks may have the same amplitude provided at least one relatively high gradient current peak is of different amplitude.

The plurality of relatively high gradient current peaks is programmed to be of relatively high current amplitude. The amplitude is preferably programmable on a computer which controls the spark generator circuit. The amplitude is programmed to suit a particular analytical application. Typically, the current amplitude of at least some, more preferably most, most preferably all, of the plurality of peaks is between 15 and 250 A, more typically between 20 and 150 A.

Between adjacent peaks of different amplitude, the current step (i.e. difference in amplitude) is preferably in the range 1 to 235 A, more preferably at least 10 A, still more preferably 10 to 40 A.

The rise time of the relatively high gradient peaks may be determined generally by equation (1):

$$dI/dt = (U_{ps} - U_{arc})/L \quad (1)$$

where dI/dt is the rate of current rise, is the power supply voltage for the spark generator circuit, $U_{arc}$ is the spark voltage (e.g. 30-40 volts) and L is the peak current source inductor value (e.g. ~8 μH) of the inductor in the spark circuit. The peak duration is the sum of the rise time and fall time of the current peak, where the fall time is determined generally by equation (2):

$$dI/dt = -U_{arc}/L \qquad (2)$$

The relatively high gradient peaks may have a gradient on their rise side in the range 10-60 A/μs, preferably 25-55 A/μs, more preferably 30-50 A/μs, e.g. 40 A/μs.

The first portion (i.e. relatively high current portion) of the waveform preferably comprises an underlying current envelope i.e. comprising a current rise and a current fall. In such embodiments, the current rise may be modulated by a plurality of relatively high gradient peaks of increasing amplitude and/or the current fall may be modulated by a plurality of relatively high gradient peaks of decreasing amplitude. In other embodiments, other modulations are possible. For example, in some embodiments, only the current rise of the first portion of the waveform may be modulated by a plurality of the relatively high gradient peaks (preferably of increasing amplitude) with the current fall not having a plurality of relatively high gradient peaks, or vice versa. Preferably, at least the current rise of the first portion of the waveform is modulated by a plurality of the relatively high gradient peaks of variable amplitude and/or inter-peak duration (preferably of increasing amplitude).

The rise time for the leading edge of the first, high current modulated portion of the waveform, i.e. the rise time from the start of the spark to the highest amplitude peak, is preferably in the range 10 to 100 μs, more preferably 20 to 90 μs, e.g. 25 to 75 μs).

The first modulated relatively high current portion of the waveform is preferably of relatively short duration (i.e. as compared to the second, relatively low current portion). The duration of the modulated relatively high current portion of the waveform is preferably in the range 10 to 200 μs, more preferably 20 to 100 μs. Whilst it is generally preferable that the first modulated portion of the waveform be shorter than the second modulated portion, in some embodiments the second modulated portion of the waveform may be shorter than the first modulated portion (e.g. a first portion of 100 μs duration with a shorter second portion of 50 μs duration).

The duration of the modulated relatively low current portion of the waveform is preferably in the range 1 to 3000 μs, more preferably 50 to 2000 μs and is preferably, although not necessarily, of longer duration than the first modulated portion.

However, for some applications the second modulated portion of the waveform may not be needed. Accordingly, in an additional aspect, the present invention provides a spark generator for generating a spark for optical emission spectroscopy, wherein the spark has a current waveform comprising a modulated portion which comprises a plurality of relatively high current and high gradient peaks of variable amplitude and/or inter-peak duration. In the additional aspect of the present invention, the current waveform preferably does not comprise a modulated portion of relatively low current and low gradient which is substantially without modulated peaks.

The term inter-peak duration herein means the duration between adjacent peaks as measured peak-to-peak. The term variable inter-peak duration in relation to the plurality of relatively high gradient current peaks means peaks that are not all of the same inter-peak duration, i.e. are not all evenly spaced apart in time. The inter-peak duration of the peaks may be independently adjusted, e.g. according to a modulation program. For example, the inter-peak duration of the peaks may be dependent on one or more reference currents of a modulation program, as described in detail below. The inter-peak duration of the plurality of relatively high gradient peaks is preferably in the range 1 to 100 μs.

The relatively low current second modulated portion of the waveform is substantially without any modulated peaks. In other words, the second modulated portion may have some minor peaks. However, preferably, second modulated portion is without any modulated peaks, i.e. no modulated peaks at all.

The relatively low current second portion is preferably substantially flat (i.e. substantially not sloping) over most of its duration. In that case, the second portion is not a vanishing current but a stabilised and controlled current. The low gradient modulation of the relatively low current second portion preferably modulates the current toward a current plateau.

The average current amplitude of the modulated relatively low current portion is preferably in the range 1 to 60 A, more preferably 5 to 50 A, more preferably 10 to 40 A.

The low gradient of the second modulated portion of the waveform preferably has a current gradient not more than about 1 A/μs, more preferably not more than about 0.5 A/μs and most preferably not more than about 0.2 A/μs. Typically, the low gradient of the second modulated portion of the waveform preferably has a current gradient from about 0.1 to about 1 A/μs. The amplitude of the second modulated portion of the waveform is preferably programmable in a controller which controls the spark generator circuit.

In some embodiments, the low gradient modulation of the second relatively low current portion may be stopped after a pre-determined time such that the low current portion then follows an unmodulated decay, e.g. an exponential decay.

The current waveform is preferably terminated abruptly, e.g. by a short circuit of the current source. Advantageously, this reduces afterglow arcing. The interruption can be clearly seen on the current waveform shown in FIG. 1 at point SC.

The second relatively low current portion of the waveform is of relatively long duration (i.e. as compared to the first relatively high current portion). The duration of the second relatively low current portion is programmable as is the rest of the waveform. Typically, the duration of the second modulated low current portion is 1 to 3000 μs, more preferably 50 to 2000 μs.

The overall duration of the spark, or waveform width, is also preferably programmable. Typically, the spark waveform duration is in the range 100 to 3200 μs, more typically 100 to 2100 μs (e.g. about 500 μs).

The spark generator is arranged to form a spark in a spark gap. The spark gap is preferably formed between an electrode and the sample to be analysed. Accordingly, the spark generator preferably comprises an electrode and a sample support arranged to form a spark gap between said electrode and a sample mounted on said sample support to be analysed so that the spark is formed in said spark gap. The spark is preferably formed in an inert, e.g. argon, atmosphere as is conventional, e.g. the electrode, sample support and sample may be located in a spark chamber which can be flushed with an, e.g., argon atmosphere. The spark is formed by discharge of at least one current source, e.g. an electrical circuit, preferably an RLC circuit. One or more discharge circuits or current sources for spark OES can be employed under the control of a program to modulate the discharge waveform in accordance with the present invention. The spark waveform may be formed from the discharge of two or more circuits or current sources, e.g. as described in EP 396 291 B1, e.g. comprising a circuit for high current and a circuit for low current or as described with reference to FIG. 5B below. In this way, the spark may be generated from one, two or more current sources. The spark generator preferably comprises at last one, preferably two, high voltage RLC circuit(s) arranged to form the spark in the spark gap upon discharge of the circuit(s), wherein the circuit(s) comprises means for modulating the waveform of the spark, i.e. in accordance with the present invention. That is, the or each current source for generating the spark preferably comprises a high voltage RLC circuit arranged to form the spark in the spark gap upon discharge of the circuit.

The spark generator for generating the spark is preferably computer controlled and thus programmable. Accordingly, the current waveform is programmable. The computer for controlling the spark generator is preferably conveniently the same computer that controls other features of the spectrometer such as processing data from the detecting system though it might be a separate computer, e.g. a dedicated processor associated with the spark-forming electronics. The spark generator preferably comprises a (i.e. one or more) high voltage RLC circuit and the spark is generated from the discharge of the circuit in a known way. However, the discharge is modulated to produce the waveform according to the present invention. Methods of modulating such circuits are known in the art and further methods are described below.

Preferably, a program is stored and run on a computer which controls the at least one current source (e.g. circuit) and modulates the discharge of the source to produce a spark having a waveform according to the present invention. The program defines the current waveform to be employed for the spark including any modulated and unmodulated portions, e.g. in terms of the peak amplitude, inter-peak duration, and/or number of peaks in the first, relatively high current portion, the amplitude, gradient and/or duration of the modulated second relatively low current portion, the total spark time and optionally other aspects of the waveform (e.g. any unmodulated portions and/or short circuit termination). The computer may store a number of different set programs or at least one variable program, each program or variation of program defining a slightly different current waveform, and either a user or the computer may select the program most suitable for a given analytical application. The computer may store one or more programs for modulating the waveform wherein there are variables representing, e.g., the amplitude, inter-peak duration and number of the peaks, and durations of the relatively high current portion and relatively low current portion.

The invention may be effected, for example, by one or more suitable programmable current sources for generating a spark. Known circuits for programmable current sources for generating sparks are described in and shown in FIGS. 2A, 2B and 3 of EP 396 291 B1, the contents of which is hereby incorporated by reference in its entirety. It will be appreciated that the circuits described in EP 396 291 B1 are capable of being controlled according to a program stored and run on the computer which controls the circuits. The or each circuit may be provided, for example, with appropriate components to enable the discharge (spark) current to be modulated, e.g. a measuring resistor, comparator and associated circuit switch component(s), as described in EP 396 291 B1. Accordingly, the present invention preferably comprises: current measuring means for measuring the spark current, current comparing means for comparing the spark current to one or more reference currents (e.g. one reference current for each programmable current source) and current adjusting means for adjusting the current from the or each programmable current source, i.e. in response to comparing the spark current to the one or more reference currents. The amplitude and/or inter-peak duration of the peaks of the first modulated portion of the waveform may thus be adjusted, e.g. dependent on the one or more reference currents.

Figure 5A:
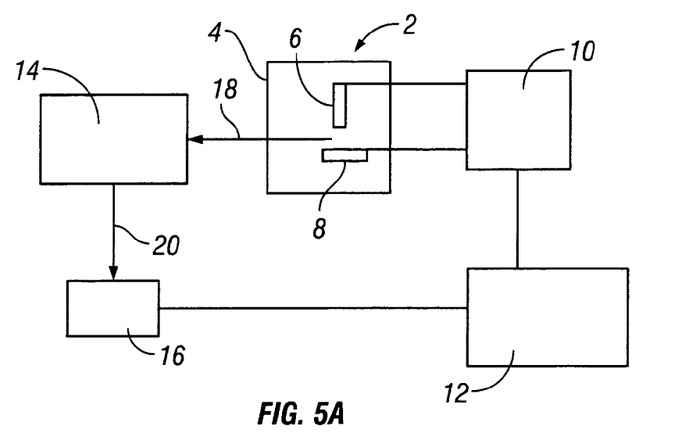
FIG. 5A shows schematically an embodiment of an optical emission spectrometer according to the present invention.
Figure 5B:
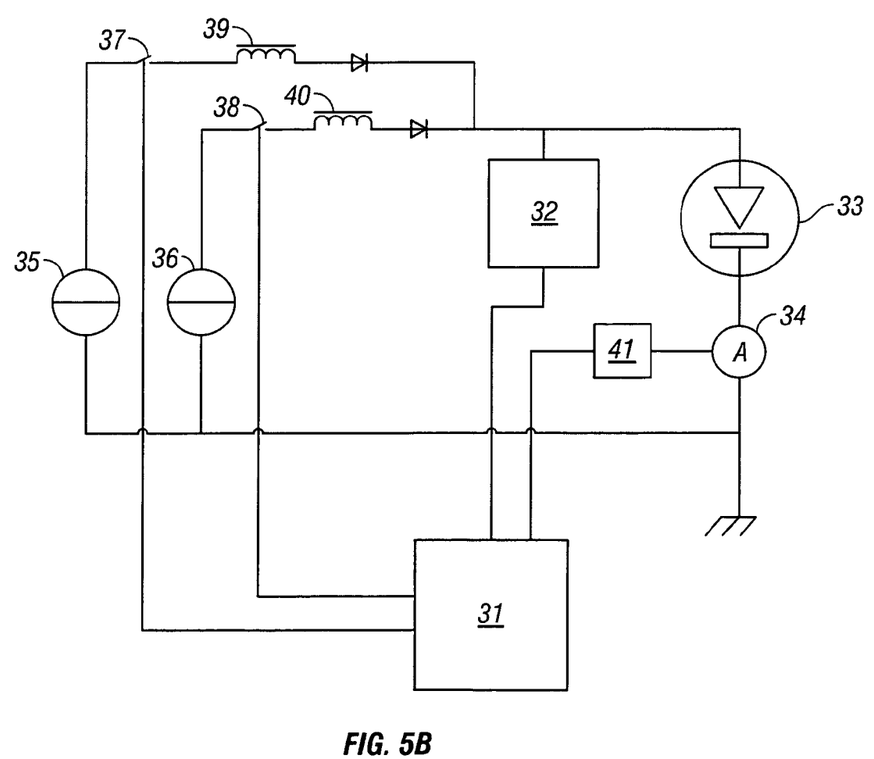
FIG. 5B shows schematically an embodiment of a circuit arrangement for a spark generator according to the present invention.

A preferred circuit for the spark generator according to the present invention is shown in FIG. 5B and described below. The or each circuit for a programmable current source preferably comprises modulating means comprising current measuring means for measuring the spark current (e.g. a measuring resistor), current comparing means (e.g. comparator or Field Programmable Gate Array (FPGA)) for comparing the spark current to a reference current and current adjusting means (e.g. a switch) for adjusting the current flow from the or each programmable current source. A preferred arrangement of modulating means for the modulation of the current source(s) comprises a current measuring means for measuring the spark current, an analogue-to-digital (A/D) converter for converting the measured current to digital form, a FPGA for receiving the measured current (or signal representative thereof) in digital form and associated circuit switch component(s) (e.g. IGBT or power transistor) controllable by the FPGA in accordance with a modulation program for adjusting the current flow from the programmable current source. The FPGA compares the measured current with reference currents for the or each programmable current source and operates the associated circuit switch component(s) accordingly to modulate the current flow from the or each current source. The reference current(s) vary with respect to the spark time so as to produce a current waveform in accordance with the present invention.

The present invention preferably employs at least one current source, current measuring means (e.g. a measuring resistor) in the spark generator for measuring the spark current during the spark, current comparing means (e.g. comparator or FPGA etc.) for comparing the spark current to a reference current (e.g. the reference being provided via a digital to analogue (D/A) converter by a computer in accordance with the modulation program in the case of an analogue comparator) and current adjusting means (e.g. a circuit switch, which is preferably a variable switch such as a variable amplifier element, e.g. a FET, IGBT or power transistor) for adjusting the spark current to a pre-determined value dependent on the reference current. The reference is usually an ideal current value stored in the computer, which is a function of the voltage from the e.g. D/A. Accordingly, it will be appreciated that comparing of the currents may actually involve comparing voltages representing the currents. Likewise, the term reference current herein includes both a reference current and a reference voltage or other signal representing a reference current.

Where two or more programmable current sources are employed, each current source may be modulated by a separate (i.e. its own) current measuring means, current comparing means and current adjusting means, as well as being supplied with a separate reference current (or reference voltage representing the reference current). Alternatively, where two or more current sources (e.g. circuits) are employed, each current source may be modulated by a single current measuring means and current comparing means (e.g. FPGA) but have separate (i.e. their own) current adjusting means (e.g. switches), as well as there being separate reference currents for each current source. The sampling frequency (modulation frequency) for comparing the spark current to a reference current defined by the computer program for adjusting the spark current if necessary is preferably at least 5 MHz. That is, the modulation frequency for modulating the current waveform is preferably at least 5 MHz. In this way a considerable number of relatively high gradient peaks of variable amplitude and/or inter-peak duration may be produced within the first high current portion of the waveform to provide greater control of the spark energy.

More preferably, the spark generator has at least two (most preferably two) modulated (i.e. programmable) current sources, including a high current source and a low current source, e.g. as shown in FIG. 5B herein and described below. The high current source is preferably a fast rise time high current source. The modulated high current source preferably can produce a high current, e.g. with a gradient of 40 A/µs and a current maximum of 250 A. The discharge of the high current source is preferably for generating the amplitude and inter-peak duration modulated peaks of the first relatively high current portion. The modulated low current source discharge preferably can produce a low current with low rise time, e.g. with a gradient of 4 A/µs and a current maximum of 50 A. The low current source is preferably for generating the second relatively low current portion, where more precision is needed. The high and low current sources preferably each comprise a modulated RLC circuit. The values of the resistance and/or the inductance of each RLC circuit are suitably chosen to provide the required high and low current characteristics of the waveform as described. The high and low current sources preferably have a common power supply and capacitor. Preferably, both the modulated high and low current sources are enabled from the start of the spark, e.g. after a trigger signal, so the current waveform overall is the sum of both modulated currents. The high current source typically stops before the low current source stops. Optionally, the modulation of the low current source can be discontinued at a time after stopping the high current source so that a natural current decay occurs from that time. Optionally, a current short-circuit can be employed to terminate the low current source abruptly. The sampling or modulation frequency for modulating the high current source and the low current source is preferably at least 5 MHz. Accordingly, preferably the spark is generated from two or more programmable current sources, more preferably a programmable high current source and a programmable low current source and even more preferably the first modulated portion is generated by the programmable high current source and the second modulated portion is generated by the programmable low current source.

The spark generator of the present invention is for use in a spark optical emission spectrometer. The spark generator generates the spark for exciting the elements in the sample to emit light. A spark optical emission spectrometer according to the present invention preferably further comprises, in addition to the spark generator according to the present invention: an optical system for dispersing the emitted light from the sample, i.e. into discrete wavelengths or spectral lines, a detection system for detecting the light intensity of the dispersed light and a data storage and processing system (e.g. a computer) for storing and processing signals from the detection system representing the light intensity.

FIG. 5A shows schematically one embodiment of an optical emission spectrometer for implementing the present invention. The spectrometer is non-limiting on the scope of the invention and is for illustration only. The spectrometer is controlled by a computer 12. The computer 12 stores one or more programs for modulating the discharge of a spark source 10 with a waveform in accordance with the present invention. The spark source 10 comprises two high voltage RLC circuits (not shown). More specifically, the spark source 10 comprises a high current source and a low current source, each comprising components to enable the discharge (spark) current to be modulated, e.g. a current measuring means, comparator or FPGA and associated circuit switch components. In use, a type of feedback system is therefore employed in the spark source 10 involving providing the discharge current to the, e.g., comparator or FPGA which is also fed with reference currents from the computer in accordance with the computer program, and switches in the circuits are actuated to either allow current flow or reduce current flow in accordance with the program to provide the modulated currents from each current source which together make up the current waveform of the invention. Each of the high and low current sources is provided with a separate reference current. The source 10 is electrically connected to electrode 6 and sample 8 housed inside an argon-filled spark chamber 4 so that, in use, a spark is formed between them to vaporise and excite a portion of the sample 8 upon discharge of the circuit. The sample 8 is typically a metal sample and is typically in the form of a disc. In use, light 18 containing spectral lines emitted by the elements in the sample 8 upon spark excitation enters optical system 14 which disperses the light into spectral lines. The optical system 14 typically comprises a diffraction grating (not shown) for dispersing the light. Selected dispersed spectral lines 20 are then detected by means of detecting system 16 which comprises one or more photodetectors, e.g. photomultiplier tube or CCD detector. The signals from the detecting system 16, optionally after further processing, are received by the computer 12 which stores and processes them as data for ultimate output, e.g. in the form of a spectrum or other qualitative or quantitative analysis of the sample. The optical system 14 and detection system 16 are typically held under a reduced pressure (vacuum) and/or flushed with an optically inert gas to avoid interference with the spectral lines.

A preferred circuit arrangement for the spark source of FIG. 5A is shown in FIG. 5B. Referring to FIG. 5B, a high current source 35 and a low current source 36 are shown, which utilise a common power supply e.g. 350 V (not shown) and capacitor e.g. 220 µF. The high and low current sources 35 and 36 are each connected in a circuit via respective IGBT transistor switches 37 and 38 and inductors 39 and 40 respectively across a spark gap 33. The values of the inductance and resistance in each circuit are chosen to provide the high current and low current, e.g. 4 µH for the high current portion and 360 µH for the low current portion. Current flowing across the spark gap 33 is measured with a current measuring device 34 and the measured current is provided via ND converter 41 to a Field Programmable Gate Array (FPGA) and controller 31. The FPGA and controller 31 compares the measured current with reference currents for each of the high and low current sources supplied from the computer 12 (shown in FIG. 5A). The comparison is made at a frequency of at least 5 MHz and the switches 39 and 40 are independently opened or closed depending on whether the measured current is greater or less than the respective reference value thereby to produce the spark current waveform according to the present invention. An ignition device 32 is triggered by the FPGA in accordance with instructions from the computer 12 to start the spark. The ignition device may be of the type described for the circuit initiator in EP 396 291 (FIG. 3 therein). In use, typically both the high and low modulated current sources are enabled from the start of the spark, e.g. after the trigger signal, so the current waveform overall is the sum of both modulated currents. The high current source is the typically stopped after a specified time and before the low current source stops. Alternatively, the high and low current sources may be started at different times. For example, the high current source may be triggered from the start and after a specified time delay the low current source may start, the two current sources overlapping before the high current source is stopped and the low current source continued. Optionally, the modulation of the low current source can be discontinued at a time after stopping the high current source so that a natural current decay occurs from that time. Typically, a current short-circuit is employed to terminate the low current source abruptly.

According to a further aspect of the present invention there is provided a method of optical emission spectroscopy comprising:

generating a spark between an electrode and a sample to be analysed using a spark generator according to the present invention;

dispersing light emitted by the sample as a result of the spark; and detecting the intensity of the dispersed light at selected wavelengths.

The method of optical emission spectroscopy according to the present invention typically comprises generating a large number of sparks in series and collecting light intensity data resulting from successive sparks in the series to accurately determine a composition. The number, duration and frequency of the sparks depends on the analytical application. The number of sparks employed in the method for a composition determination is typically in the range 1,000 to 5,000, with the total duration of each individual spark (i.e. total of the high and low current portions) typically lasting from 100 to 2000 μs (e.g. about 500 μs). The spark frequency is typically in the range 1 to 1000 Hz, more typically 100 to 600 Hz. The overall sparking time for the method (i.e. time taken for all sparks) is typically 3 to 30 seconds.

The spark generator need not generate a series of sparks all with the same waveform but the spark series may contain sparks with different waveforms according to the present invention in order to better suit a particular analytical application. For instance, one waveform may be chosen to suit analysis of one element and another waveform may be chosen to suit analysis of another element. For example, one spark type may have a modulation with, e.g., a given number of peaks and given peak frequency in the first modulated high current portion of the waveform and another spark type, which could be alternated for example with the first spark type, may have a different modulation, e.g. a different number of peaks and/or peak frequency in the modulated high current portion. Any number of different spark waveforms may be employed in the spark series and these may be employed in any sequence or combination. Preferably, where sparks with more than one spark waveform are employed for a given analytical application, each waveform is preferably a waveform according to the present invention. However, it is possible that sparks having a waveform according to the present invention could be combined in a sequence with sparks having waveforms other than those of the present invention.

One or more other steps of OES methods may be used with the method of the present invention as are conventional, e.g. storing the intensity of the detected light as data, optionally processing said data; outputting said data optionally after said processing; and/or determining an elemental composition of the sample.

The measurement of the emitted light intensity may be performed during delivery of at least one or preferably both of the first and the second modulated portions of the current (i.e. preferably during a time window in which both the first and the second modulated portions of the current are delivered), depending on the excitation energy of the specific emission line.

Figure 6A:
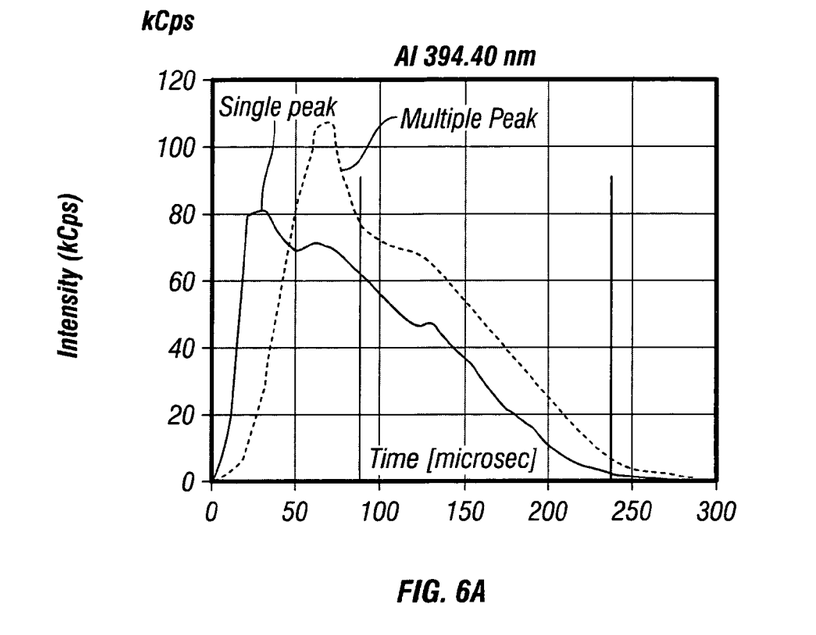
FIG. 6A shows intensity-time plots recorded on an optical emission spectrometer for the Al 394.40 nm spectral line using both a prior art spark and a spark according to the present invention.
Figure 6B:
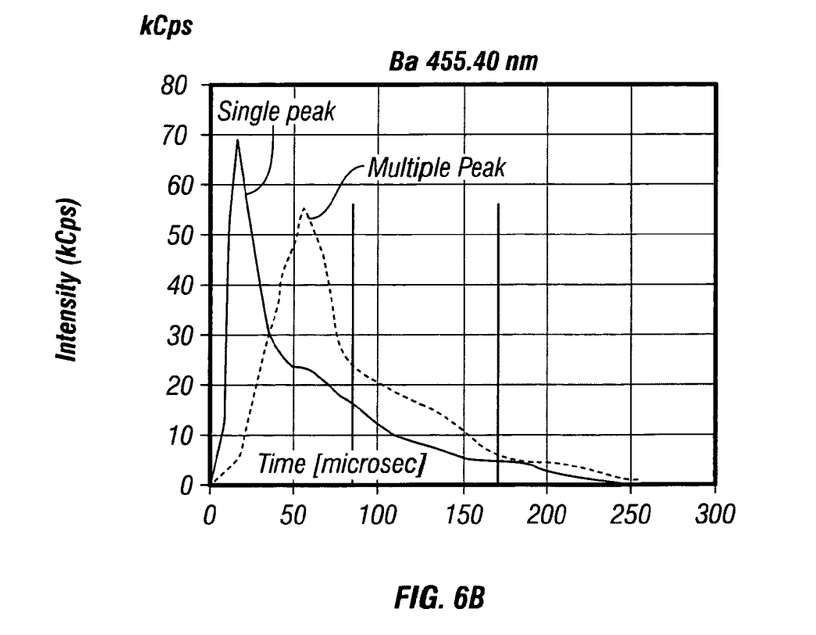
FIG. 6B shows intensity-time plots recorded on an optical emission spectrometer for the Ba 455.40 nm spectral line using both a prior art spark and a spark according to the present invention.

The present invention has been found to be of benefit to the use of so-called "time-resolved spectroscopy" (TRS) or more specifically "time gated acquisition" (TGA) in OES in which the emitted light is measured only within a defined time window located within the spark duration. Different time windows can be employed in TRS for different spectral lines. The choice of time window depends on the parameters of the spectral line such as its energy. The time window can also be chosen to minimise perturbations to the spectral line from, e.g., the source or spectral background interference. TRS is, for example, of significant benefit for trace element analysis. The present invention has been found to make the TRS even more effective. For example, referring to FIGS. 6A and 6B, there are shown intensity-time plots recorded on an optical emission spectrometer for two different spectral lines: Al 394.40 nm (FIG. 6A) and Ba 455.40 nm (FIG. 6B). For each spectral line there is an optimum time window during the spark in which to measure the intensity of the line. These time windows are shown in the Figures as the time between the vertical lines drawn on the plots. For each spectral line, there is shown an intensity-time plot recorded using sparks having a prior art current waveform with a single high current peak followed by a low current plateau (labelled "single peak") and an intensity-time plot recorded using sparks having a current waveform according to the present invention (labelled "multiple peak"). The sparks generated according to the present invention were modulated in such a way that a similar total energy was delivered to the spark as for the prior art spark but with a different amplitude-time profile. In the case of the sparks according to the present invention, it can be seen that during the optimum time window for measuring the respective spectral line, the intensity is significantly higher than with the sparks having the prior art waveform.

The invention enables determination with good precision of both trace elements and alloying elements in metal samples, in contrast to the prior art methods described above which are better suited to either one of these applications or the other.

The present invention has been found to significantly improve precision in the quantitative determination of many compositions (for a given acquisition time) and thereby reduce the acquisition time for a given precision. The improvement in acquisition time, for example, has been found to be between 10% and 50% compared to using a prior art single peak spark. The Table below shows a comparison of results acquired using a spark generator of the present invention and a prior art spark generator producing a single high current peak followed by a low current decay. The results show the acquisition times for calibrating and measuring samples in different matrices.

| Matrix | Acquisition Time [s] | | Relative Change |
|---|---|---|---|
| | Single peak spark (Prior art) | Multi-peak spark (Invention) | |
| Fe | 28.5 | 25.5 | −11% |
| Cu | 39.5 | 17.5 | −56% |
| Ni | 32.5 | 25.5 | −22% |
| Co | 32.5 | 25.5 | −22% |
| Average of matrices | 33.3 | 23.5 | −29.4% |

The use of a spark having a waveform in accordance with the present invention can reduce the rate of deterioration of the response of a CCD light detector in the environment of an OES instrument. With reference to FIG. 5A, the optical system 14 and detection system 16 are typically held under a reduced pressure (vacuum) and/or flushed with an optically inert gas to avoid interference with the spectral lines. Nevertheless, small amounts of volatile organic molecules may remain in the gaseous environment of the optical and detection system. Without being bound by any theory, it is believed by the inventors that a deterioration in the response of a CCD detector over time is due to a photochemical reaction ("quenching") of such organic molecules with intense UV light, such as may be produced when using the prior art digital spark sources. The photochemically produced products are then thought to become deposited on the surface of the phosphorus coating of the CCD detector, which lowers the detector sensitivity over time. It is understood that the spark source waveform of the present invention which spreads the energy over a plurality of peaks, rather than a single intense peak as with prior art digital spark sources, results in an observed reduced quenching probability and hence deposition rate on the detector.

Unless the context clearly indicates otherwise, as used herein plural forms of the terms herein are to be construed as including the singular form and vice versa.

Any steps in a process described herein may be performed in any order, unless stated otherwise or unless the context clearly requires otherwise.

Throughout the description and claims of this specification, the words "comprise", "including", "having", "contain" and the like and variations of the words, for example "comprising" and "comprises" etc, mean "including but not limited to", and are not intended to (and do not) exclude other components.

The use of examples, or exemplary language (including "for instance", "such as", "for example" and similar phrases) herein, is intended merely to better illustrate the invention and does not indicate a limitation on the scope of the invention unless otherwise claimed. No language in the specification should be construed as indicating any non-claimed element as essential to the practice of the invention.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention claimed is:

1. A spark generator for generating a spark for optical emission spectroscopy (OES), wherein the spark is generated from two or more programmable current sources controlled by a computer and has a programmable current waveform comprising a first modulated portion which comprises a plurality of relatively high current and high gradient peaks of variable amplitude and/or inter-peak duration and a second modulated portion of relatively low current and low gradient which is substantially without modulated peaks, wherein the amplitude and/or inter-peak duration of the peaks are programmable on the computer and can be independently adjusted according to a modulation program.

2. A spark generator as claimed in claim 1 wherein the second modulated portion tends toward a current plateau.

3. A spark generator as claimed in claim 1 wherein the first modulated portion is modulated by three or more peaks of variable amplitude and/or inter-peak duration.

4. A spark generator as claimed in claim 1 wherein the first modulated portion comprises a current rise which is modulated by a plurality of relatively high gradient peaks of increasing amplitude.

5. A spark generator as claimed in claim 4 wherein the first modulated portion comprises a current fall after the current rise which is modulated by a plurality of relatively high gradient peaks of decreasing amplitude.

6. A spark generator as claimed in claim 5 wherein the current amplitude of at least some of the plurality of peaks is between 15 and 250 A.

7. A spark generator as claimed in claim 5 wherein the inter-peak duration of the plurality of relatively high gradient peaks is in the range 1 to 100 µs.

8. A spark generator as claimed in claim 1 wherein the first modulated portion is modulated by at least a plurality of relatively high gradient peaks of a first high amplitude and a plurality of relatively high gradient peaks of a second high amplitude.

9. A spark generator as claimed in claim 1 wherein the second modulated portion is of longer duration than the first modulated portion.

10. A spark generator as claimed in claim 9 wherein the duration of the first modulated portion of the waveform is in the range 10 to 200 µs.

11. A spark generator as claimed in claim 9 wherein the rise time from the start of the spark to the top of the highest amplitude peak, is in the range 10 to 100 µs.

12. A spark generator as claimed in claim 9 wherein the average current amplitude of the second modulated portion is in the range 1 to 60 A.

13. A spark generator as claimed in claim 9 wherein the second modulated portion of the waveform has a current gradient between 0.1 and 1 A/µs.

14. A spark generator as claimed in claim 1 wherein the second modulated portion is followed by an unmodulated decay of the current.

15. A spark generator as claimed in claim 1 wherein the spark is terminated by a short circuit of one or more current sources of the spark.

16. A spark generator as claimed in claim 1 wherein the spark is generated from a programmable high current source and a programmable low current source.

17. A spark generator as claimed in claim 16 wherein the first modulated portion is generated by the programmable high current source and the second modulated portion is generated by the programmable low current source.

18. A spark generator as claimed in claim 1 wherein a modulation frequency for modulating the current waveform is at least 5 MHz.

19. A spark generator according to claim 1 wherein the second modulated portion is without any modulated peaks.

20. A method of optical emission spectroscopy comprising:
generating a spark between an electrode and a sample to be analysed using a spark generator wherein the spark is generated from two or more programmable current sources controlled by a computer and has a programmable current waveform comprising a first modulated portion which comprises a plurality of relatively high current and high gradient peaks of variable amplitude and/or inter-peak duration and a second modulated portion of relatively low current and low gradient which is substantially without modulated peaks, wherein the amplitude and/or inter-peak duration of the peaks are independently adjusted according to a modulation program.

21. A spark generator for generating a spark for optical emission spectroscopy (OES), wherein the spark is generated from two or more programmable current sources and has a current waveform comprising a first modulated portion which comprises a plurality of relatively high current and high gradient peaks of variable amplitude and/or inter-peak duration and a second modulated portion of relatively low current and low gradient which is substantially without modulated peaks, wherein the inter-peak duration and/or the amplitude of the peaks of the first portion are independently adjustable according to a modulation program.

22. A spark generator according to claim 21 wherein the inter-peak duration and/or the amplitude of the peaks are dependent on one or more reference currents of a modulation program.

23. A spark generator as in claim 21, wherein the first modulated portion of the current waveform includes a series of multiple successively increasing peak currents.

24. A spark generator as in claim 23, wherein the first modulated portion of the current waveform additionally includes a series of multiple successively decreasing peak currents, the series of multiple decreasing peak currents occurring in time after the series of multiple increasing peak currents.

25. A spark generator as in claim 21, wherein the first modulated portion of the current waveform includes a first series of multiple peak currents of a substantially first magnitude over time.

26. A spark generator as in claim 25, wherein the first modulated portion of the current waveform includes a second series of multiple peak currents of a substantially second magnitude.

27. A spark generator as in claim 21, wherein the first modulated portion of the current waveform includes a first peak current followed by a first valley current followed by a second peak current;

wherein the first valley current is smaller in magnitude than the first peak current; and wherein the second peak current is greater in magnitude than both the first peak current value and the first valley current.

28. A spark generator as in claim 21, wherein the two or more programmable current sources includes: a first programmable current source and a second programmable current source, the second programmable current source switched independently of the first programmable current source in accordance with the modulation program to produce the current waveform; and the spark generator further comprising: a controller that controls switching of both the first programmable current source and the second programmable current source to produce the current waveform.

29. A spark generator as in claim 28 further comprising:

a current measuring device to measure current used to produce the spark, the current generated by the two or more programmable current sources; and wherein the controller receives feedback of the measured current from the current measuring device, the controller utilizing the feedback to control the current generated by the two or more programmable sources in accordance with the modulation program.

30. A spark generator as in claim 21 further comprising:

a spark gap, the spark passing through the spark gap;

a current measuring device to measure current used to produce the spark across the spark gap, the current generated by the two or more programmable current sources; and a controller, the controller receiving feedback of the measured current from the current measuring device, the controller utilizing the feedback of the measured current to control the current generated by the two or more programmable sources in accordance with the modulation program.

* * * * *